(12) United States Patent
Doyen et al.

(10) Patent No.: US 11,987,764 B2
(45) Date of Patent: May 21, 2024

(54) COMPOUND COMPRISING POLYAMINE, ACIDIC AND BORON FUNCTIONALITIES AND ITS USE AS A LUBRICANT ADDITIVE

(71) Applicant: TOTALENERGIES ONETECH, Courbevoie (FR)

(72) Inventors: Valérie Doyen, Solaize (FR); Modestino De Feo, Solaize (FR); Gregory Chao, Solaize (FR)

(73) Assignee: TOTALENERGIES ONETECH, Courbevoie (FR)

( * ) Notice: Subject to any disclaimer, the term of this patent is extended or adjusted under 35 U.S.C. 154(b) by 66 days.

(21) Appl. No.: 17/775,358

(22) PCT Filed: Nov. 5, 2020

(86) PCT No.: PCT/EP2020/081065
§ 371 (c)(1),
(2) Date: May 9, 2022

(87) PCT Pub. No.: WO2021/089671
PCT Pub. Date: May 14, 2021

(65) Prior Publication Data
US 2022/0389346 A1 Dec. 8, 2022

(30) Foreign Application Priority Data

Nov. 7, 2019 (EP) .................................... 19315135

(51) Int. Cl.
*C10M 159/12* (2006.01)
*C07C 211/14* (2006.01)
*C10M 159/20* (2006.01)
*C10N 40/25* (2006.01)

(52) U.S. Cl.
CPC ......... *C10M 159/12* (2013.01); *C07C 211/14* (2013.01); *C10M 159/20* (2013.01); *C10M 2203/003* (2013.01); *C10N 2040/25* (2013.01)

(58) Field of Classification Search
CPC .............. C10M 159/12; C10M 159/20; C10M 2203/003; C07C 211/14; C10N 2040/25
See application file for complete search history.

(56) References Cited

U.S. PATENT DOCUMENTS

| 11,111,452 | B2 * | 9/2021 | Rogues De Fursac | ...................... C10M 159/12 |
| 11,242,497 | B2 * | 2/2022 | Rogues De Fursac | ...................... C10M 169/04 |
| 11,292,983 | B2 * | 4/2022 | Doyen | ...................... C07F 5/04 |
| 2007/0214713 | A1 * | 9/2007 | Karl | ...................... C10M 133/56 44/432 |
| 2015/0299606 | A1 * | 10/2015 | Muir | ...................... C10M 159/20 44/314 |

FOREIGN PATENT DOCUMENTS

WO 2018/220007 A1 12/2018

OTHER PUBLICATIONS

Dec. 18, 2020 International Search Report issued in International Patent Application No. PCT/EP2020/081065.
May 10, 2022 International Preliminary Report on Patentability issued in International Patent Application No. PCT/EP2020/081065.

* cited by examiner

Primary Examiner — Ellen M McAvoy
(74) Attorney, Agent, or Firm — Oliff PLC

(57) ABSTRACT

A product resulting from the reaction of at least: a hydroxybenzoic acid, optionally substituted by a hydrocarbyl group, or an alkali and/or alkaline earth metal salt thereof, a boron compound, a polyalkylamine component selected from triamine and tetramine compounds. Also, a lubricant composition including this product. Use of this product as a lubricant for two-stroke marine engines and four-stroke marine engines, more preferably two-stroke marine engines.

20 Claims, No Drawings

COMPOUND COMPRISING POLYAMINE, ACIDIC AND BORON FUNCTIONALITIES AND ITS USE AS A LUBRICANT ADDITIVE

The invention is directed to the reaction product of an acidic organic compound or a salt thereof, a boron compound and a polyalkylamine component selected from triamine and tetramine compounds. It is also directed to a lubricant composition comprising this reaction product, a method for its production and its uses.

STATE OF THE ART

One of the primary functions of lubricants is to decrease friction. Frequently, however, lubricating oils need additional properties to be used effectively. For example, lubricants used in large diesel engines, such as, for example, marine diesel engines, are often subjected to operating conditions requiring special considerations.

The marine oils used in low-speed two-stroke crosshead engines are of two types. On the one hand, cylinder oils ensuring the lubrication of the cylinder-piston assembly and, on the other hand, system oils ensuring the lubrication of all the moving parts apart from the cylinder-piston assembly. Within the cylinder-piston assembly, the combustion residues containing acid gases are in contact with the lubricating oil.

The acid gases are formed from the combustion of the fuel oils; these are in particular sulphur oxides ($SO_2$, $SO_3$), which are then hydrolyzed on contact with the moisture present in the combustion gases and/or in the oil. This hydrolysis generates sulphurous ($HSO_3$) or sulphuric ($H_2SO_4$) acid.

To protect the surface of piston liners and avoid excessive corrosive wear, these acids must be neutralized, which is generally done by reaction with the basic sites included in the lubricant.

An oil's neutralization capacity is measured by its BN or Base Number, characterized by its basicity. It is measured according to standard ASTM D-2896 and is expressed as an equivalent in milligrams of potash per gram of oil (also called "mg of KOH/g" or "BN point"). The BN is a standard criterion making it possible to adjust the basicity of the cylinder oils to the sulphur content of the fuel oil used, in order to be able to neutralize all of the sulphur contained in the fuel, and capable of being converted to sulphuric acid by combustion and hydrolysis.

Thus, the higher the sulphur content of a fuel oil, the higher the BN of a marine oil needs to be. This is why marine oils with a BN varying from 5 to 140 mg KOH/g are found on the market. This basicity is provided by detergents that are neutral and/or overbased by insoluble metallic salts, in particular metallic carbonates. The detergents, mainly of anionic type, are for example metallic soaps of salicylate, phenate, sulphonate, carboxylate type etc. which form micelles where the particles of insoluble metallic salts are maintained in suspension. The usual neutral detergents intrinsically have a BN typically less than 150 mg KOH per gram of detergent and the usual overbased detergents intrinsically have a BN in a standard fashion comprised between 150 and 700 mg KOH per gram of detergent. Their percentage by mass in the lubricant is fixed as a function of the desired BN level.

Currently, in the presence of fuel oils with a high sulphur content (3.5% w/w and more), marine lubricants having a BN from 70 to 140 are used. In the presence of fuel oils with a low sulphur content (1.5% w/w and less), marine lubricants having a BN from 10 to 70 are used. In these two cases, a sufficient neutralizing capacity is achieved as the necessary concentration in basic sites provided by the neutral and/or the overbased detergents of the marine lubricant is reached.

Actually, the operating conditions of marine engine and notably of two-stroke marine engine, are increasingly stringent standards. Accordingly, the lubricant being directly in contact with the engine, and notably with the hot section of the engine as for example the segment-piston-pump assembly, shall ensure a resistance to an elevated temperature and thus, reduce or prevent the formation of deposits in the hot section of the engine but also shall ensure a good neutralization towards the sulphuric acid generated during the combustion of fuel.

There is a need for a marine detergent, which is able to be used in presence of high-sulphur fuels and also low-sulphur fuels, respectively having a BN from 70 to 140 and having a BN from 10 to 70, and having a good neutralization capacity of sulphuric acid while maintaining a good thermal resistance and thus a lower risk of deposits formation in the hot section of the engine.

There is also a need for marine lubricants having a BN, notably having a BN from 70 to 140, able to be used in presence of high-sulphur fuels and also low-sulphur fuels and having a good neutralization of sulphuric acid while maintaining a good thermal resistance and thus a lower risk of deposits formation in the hot section of the engine.

It would also be desirable to have a lubricant for marine engines, including for a two-stroke marine engine, displaying no or few risk of viscosity increase over time, and particularly during its use.

An object of the present invention is to provide a lubricant additive overcoming all or part of the aforementioned drawbacks. Another object of the present invention is to provide a lubricant additive whose formulation within lubricant compositions is easy to implement.

Another object of the present invention is to provide a lubricant composition overcoming all or part of the aforementioned drawbacks.

Another object of the present invention is to provide a method for lubricating a marine engine, and especially for lubricating a two-stroke marine engine used with both low-sulphur fuel and high-sulphur fuel.

Another object of the present invention is to provide a method for lubricating a marine engine, and especially for a two-stroke marine engine used with very low-sulphur fuel.

Another object of the present invention is to provide a method for reducing the formation of deposits in the hot section of a marine engine, notably of a two-stroke marine engine.

Document US 2015/0299606 discloses a metal-free detergent and antioxidant additive that can be used in a lubricating oil comprising the reaction product of an acidic organic compound, a boron compound, a polyamine such as polyethylene imine, and optionally an alkoxylated amine and/or an alkoxylated amide.

US 2005/172543 discloses a composition comprising the reaction product of an acidic organic compound, a boron compound and a basic organic compound and its use as a detergent additive for lubricants and hydrocarbon fuels.

EP 3 072 951 discloses a detergent composition for use in lubricating oil compositions, said detergent comprising:
  an overbased calcium sulphonate, and
  a metal free low ash detergent comprising the reaction product of:
    an acidic organic compound,
    a boron compound, and
    an amine component comprising one or more amines.

None of these documents discloses the reaction product of an acidic organic compound, a boron compound and a polyamine as defined here-under.

US 2016/0281014 discloses a lubricating oil detergent composition comprising an overbased calcium sulphonate and a low ash detergent, which is metal free and comprises the reaction product of an acidic organic compound such as an alkylated salicylic acid, a boron compound and an amine component.

EP 1 783 134 discloses a process for the preparation of middle to high TBN detergent-dispersant additives for lubricating oil applications for internal combustion engines. These additives consist in overbased alkali metal alkyl hydroxybenzoates. Such additives have lower solubility in lubricating oils and for this reason are mainly used in four-stroke slow-speed engines.

WO 2018/220009 discloses a product resulting from the reaction of at least a hydroxybenzoic acid, optionally substituted by a hydrocarbyl group, a boron compound and an amine component selected from a di-fatty-alkyl(ene) poly-alkylamines composition.

WO 2018/220007 discloses a product resulting from the reaction of at least a hydroxybenzoic acid, optionally substituted by a hydrocarbyl group, a boron compound and an amine component comprising two or three amine functions.

Additives combining an alkylated salicylic acid, a boron compound and an amine component provide satisfactory resistance to corrosion and wear. However, for some of those compounds, increasing the amount of additive in the lubricating oil increases oil viscosity while neutralization occurs, thus degrading the lubricating efficacy. Other compounds have proven satisfactory with regards to the control of oil viscosity increase but are less satisfactory with regards to detergency performance. Other compounds have also proven satisfactory with regards to the performance of detergency but are less satisfactory with regards to oil viscosity increase while neutralisation occurs.

Thus, there is a need for a lubricant additive that will simultaneously provide effective corrosion and wear resistance, that will provide satisfactory rheology while in use, in order to enhance lubricating efficacy, and that will provide high detergency performance, thus avoiding the formation of deposits.

The reaction products of the present invention advantageously provide improved detergency and oxidation stability. Furthermore, the reaction products provide excellent detergency and cleanliness to a lubricating oil and do not degrade the oil rheology under use. They provide excellent corrosion and wear resistance.

SUMMARY OF THE INVENTION

The invention concerns the reaction product of at least:
a hydroxybenzoic acid, optionally substituted by a hydrocarbyl group, or an alkali and/or alkaline earth metal salt thereof,
a boron compound,
a polyalkylamine component selected from compounds of formula (IV):

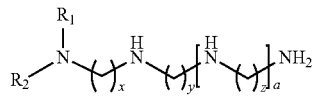

wherein:
a represents either 0 or 1;
x, y, z, represent, independently, an integer selected from 1, 2 or 3.
when a=0, $R_1$, $R_2$ represent, independently, a $C_1$-$C_3$ alkyl group,
when a=1, $R_1$, $R_2$ represent, independently, a group selected from: hydrogen, or $C_1$-$C_3$ alkyl group.

The invention is also directed to a lubricant composition comprising such a reaction product, a base oil and optionally one or more further additives.

The invention is also directed to the use of the product or the lubricant composition, for lubricating two-stroke marine engines and four-stroke marine engines, more preferably two-stroke marine engine.

According to a favourite embodiment, the hydroxybenzoic acid, optionally substituted by a hydrocarbyl group, is selected from mono-alk(en)yl substituted salicylic acids, di-alk(en)yl substituted salicylic acids, acid functionalized calixarenes, notably salicylic acid calixarenes, and mixtures thereof.

According to a more favourite embodiment, the hydroxybenzoic acid compound, optionally substituted by a hydrocarbyl group, responds to formula (I):

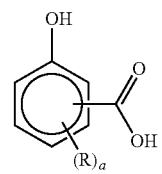

wherein:
R represents a hydrocarbyl group with 1 to 50 carbon atoms, and R can comprise one or more heteroatoms,
a is an integer, a represents 0, 1 or 2.

According to a favourite variant, in formula (I), a represents 1 or 2.

According to another variant, in formula (I), a represents 0.

According to an even more favourite embodiment, the hydroxybenzoic acid compound, optionally substituted by a hydrocarbyl group, responds to formula (IA):

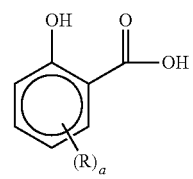

According to a favourite variant, in formula (IA), a represents 1 or 2.

According to another variant, in formula (IA), a represents 0.

According to a favourite embodiment, the boron compound is selected from: boric acid, boric acid complexes, boric oxide, a trialkyl borate in which the alkyl groups comprise independently from 1 to 4 carbon atoms, a $C_1$-$C_{12}$ alkyl boronic acid, a $C_1$-$C_{12}$ dialkyl boric acid, a $C_6$-$C_{12}$ aryl boric acid, a $C_6$-$C_{12}$ diaryl boric acid, a $C_7$-$C_{12}$ aralkyl boric acid, a $C_7$-$C_{12}$ diaralkyl boric acid, or products deriving from these by substitution of an alkyl group by one or more alkoxy unit. Advantageously, the boron compound is boric acid.

According to a favourite embodiment, the amine component is selected from compounds of formula (IVA):

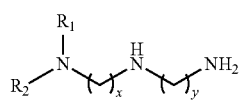

(IVA)

wherein
$R_1$, $R_2$ represent, independently, a $C_1$-$C_3$ alkyl group,
x and y are integers representing, independent of each other, either 1, 2, or 3, and
the total number of carbon atoms in (IVA) is from 4 to 10.

According to an alternative favourite embodiment, the amine component is selected from compounds of formula (IVB):

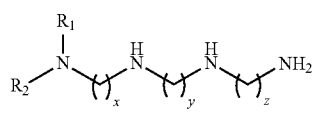

(IVB)

wherein
$R_1$, $R_2$ represent independently a group selected from: hydrogen and a $C_1$-$C_3$ alkyl group, and
x, y and z are integers representing, independently, either 1, 2, or 3.

DETAILED DESCRIPTION

The term "consists essentially of" followed by one or more characteristics, means that may be included in the process or the material of the invention, besides explicitly listed components or steps, components or steps that do not materially affect the properties and characteristics of the invention.

The expression "comprised between X and Y" includes boundaries, unless explicitly stated otherwise. This expression means that the target range includes the X and Y values, and all values from X to Y.

"Alkyl" means a saturated hydrocarbon chain, that can be linear, branched or cyclic.

"Alkenyl" means a hydrocarbon chain, that can be linear, branched or cyclic and comprises at least one unsaturation, preferably a carbon-carbon double bond.

"Aryl" means an aromatic hydrocarbon functional group. This functional group can be monocyclic or polycyclic. As examples of an aryl group one can mention: phenyl, naphtalen, anthracen, phenanthren and tetracen.

"Aralkyl" means an aromatic hydrocarbon functional group, preferably monocyclic, that comprises an alkyl chain substituent.

"Hydrocarbyl" means a compound or fragment of a compound selected from: an alkyl, an alkenyl, an aryl, an aralkyl. Where indicated, some hydrocarbyl groups include heteroatoms.

The term "alkali and/or alkaline earth metal salts thereof" used herein is used in the same way as the term "alkali and/or alkaline earth metal hydroxybenzoate compounds, optionally substituted by a hydrocarbyl group".

The term "overbased" refers to a class of metal salts or complexes. These materials have also been referred to as "basic", "superbased", "hyperbased", "complexes", "metal complexes", "high-metal containing salts", and the like. Overbased products are metal salts or complexes characterized by a metal content in excess of that which would be present according to the stoichiometry of the metal and the particular acidic organic compound reacted with the metal, for example a carboxylic acid.

The term "Total Base Number" or "TBN" refers to the equivalent number of milligrams of KOH needed to neutralize 1 gram of a product. Therefore, a high TBN reflects strongly overbased products and, as a result, a higher base reserve for neutralizing acids. The TBN of a product can be determined according to ASTM standard No. D2896 or equivalent procedure.

The Hydroxybenzoic Acid Compounds and Salts Thereof

The hydroxybenzoic acid compounds, optionally substituted by a hydrocarbyl group, are molecules that comprise at least one benzoic acid fragment, and the aromatic ring bears at least one hydroxyl function and possibly one alkyl, alkenyl, aryl or aralkyl substituent. When present, the hydrocarbyl substituent and the hydroxy function can be in ortho, meta or para position with regards to the acidic function and with regards to each other. The hydrocarbyl substituent can comprise from 1 to 50 carbon atoms.

The hydroxybenzoic acid compounds include salicylic acid (hydroxy-2-benzoic acid), hydroxy-3-benzoic acid, hydroxy-4-benzoic acid, preferably salicylic acid.

The hydrocarbyl-substituted hydroxybenzoic acid compounds include, non limitatively, mono-alk(en)yl substituted salicylic acids, di-alk(en)yl substituted salicylic acids, acid functionalized calixarenes, notably salicylic acid calixarenes, and mixtures thereof.

A calixarene is a macrocycle consisting of several phenolic units which can be para substituted and connected by a methylene bridge. This cyclic oligomer comprises a sequence of 4 to 16 phenols forming a ring and connected by methylene bridges —(CH$_2$)— or similar bridges.

The hydroxybenzoic acid compounds, optionally substituted by a hydrocarbyl group, can, according to a first variant, respond to formula (I) below:

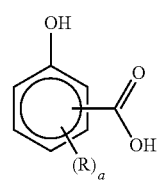

(I)

wherein:
R represents a hydrocarbyl group with 1 to 50 carbon atoms, and R can comprise one or more heteroatoms,
a is an integer, a represents 0, 1 or 2.
According to a first variant, a=0.
According to another variant, a=1 or 2.
When a=2, the two hydrocarbyl groups can be identical or different.
Advantageously, a=1.
Hydrocarbyl groups in formula (I) means alkyl, alkenyl, aryl and aralkyl groups, possibly comprising one or more heteroatoms.

Hydrocarbyl groups in formula (I) may be linear, branched or cyclic.

Heteroatoms in R can be selected from O, N, S. For example, they can be present as one or more of: an —OH, —NH$_2$, or —SH substituent, or an —O—, —NH—, —N= or —S— bridge.

Preferably, R does not comprise heteroatoms.

Preferably, R is selected from alkyl and alkenyl groups.

Advantageously, R represents an alkyl or an alkenyl group with 1 to 50 carbon atoms.

Preferably, R is selected from linear and branched alkyl and alkenyl groups.

Even more advantageously, R represents a linear alkyl group with 1 to 50 carbon atoms.

Preferably, R comprises from 12 to 40 carbon atoms, even more preferably R comprises from 18 to 30 carbon atoms.

Salicylic acid is commercially available.

Hydrocarbyl substituted hydroxybenzoic acids can be prepared according to the method disclosed in EP 1 783 134.

Advantageously, in formula (I), —OH and —COOH are in the ortho position on the phenyl ring, and the molecule of formula (I) is salicylic acid or a salicylic acid derivative of formula (IA):

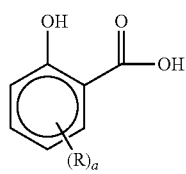

(IA)

wherein R and a have the same definition as in formula (I) and the favourite variants of these parameters are the same as in formula (I).

Hydrocarbyl substituted salicylic acids are commercially available from Chemtura under trade name RD-225 and S-220 or from Oronite under trade name OLOA 16300, OLOA 16301 and OLOA 16305 or from Infineum under trade name M7101, M7102, M7121 and M7125.

According to a second variant, the hydroxybenzoic acid compounds, optionally substituted by a hydrocarbyl group, can be selected from calixarene structures. Calixarene structures according to the invention include cyclic structures comprising m units of a hydrocarbyl-substituted hydroxybenzoic acid of formula (II) and n units of a phenol of formula (III) which are joined together to form a ring:

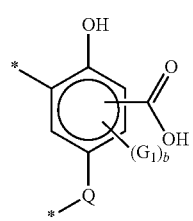

(II)

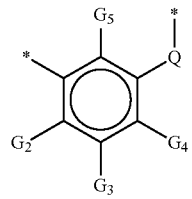

(III)

wherein
G$_1$ represents a hydrocarbyl group with 1 to 50 carbon atoms, and G$_1$ can comprise one or more heteroatoms,
b is an integer, b represents 0, 1 or 2,
Q represents independently a divalent bridging group,
G$_2$, G$_3$, G$_4$ and G$_5$, are selected from: OH, H, or a hydrocarbyl group with 1 to 50 carbon atoms that can comprise one or more heteroatoms, with the condition that one or two of G$_2$, G$_3$, G$_4$ and G$_5$ is OH,
m and n are integers that verify:
m is from 1 to 8,
n is at least 3,
m+n is from 4 to 20.

According to a variant, b represents 0.

According to another variant, b represents 1 or 2.

Advantageously, m+n is from 5 to 12.

When b=2, the two hydrocarbyl groups G$_1$ can be identical or different.

Hydrocarbyl groups in formula (II) and (III) means alkyl, alkenyl, aryl and aralkyl groups, possibly comprising one or more heteroatoms.

Hydrocarbyl groups in formula (II) and (III) may be linear, branched or cyclic.

Heteroatoms in G$_1$, G$_2$, G$_3$, G$_4$ and G$_5$ can be selected from O, N, S. For example, they can be present as one or more of: an —OH, —NH$_2$, or —SH substituent, or an —O—, —NH—, —N= or —S— bridge.

Preferably, G$_1$ is selected from alkyl and alkenyl groups.

Advantageously, G$_1$ represents an alkyl or an alkenyl group with 1 to 50 carbon atoms. Even more advantageously, G$_1$ represents a linear alkyl group with 1 to 50 carbon atoms.

Preferably, G$_1$ comprises from 12 to 40 carbon atoms, even more preferably G$_1$ comprises from 18 to 30 carbon atoms.

Preferably, the units (II) are selected from those that respond to formula (IIA) here-under:

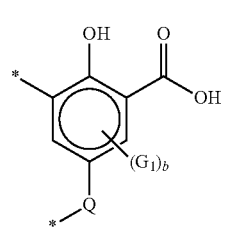

(IIA)

wherein G$_1$, Q and b have the same definition as in formula (II) and the favourite variants of these parameters are the same as in formula (II).

Advantageously, in formula (III), G$_5$ is hydroxyl.

Advantageously, G$_2$, G$_3$, G$_4$ independently represent H or an alkyl or an alkenyl group with 1 to 50 carbon atoms. More advantageously, $G_2$, $G_3$, $G_4$ independently represent H or a linear alkyl group with 1 to 40 carbon atoms.

Preferably, $G_2$, $G_3$, $G_4$ are independently selected from H and linear alkyl groups comprising from 1 to 30 carbon atoms, more preferably they are selected from H and linear alkyl groups comprising from 4 to 25 carbon atoms.

When more than one unit (II) is present, the units (II) can be identical or different.

The units (III) can be identical or different in a calixarene molecule.

When more than one unit (II) is present in the ring (m>1), the units (II) and (III) are distributed randomly.

Each Q may independently be selected from —S— and groups represented by the formula —(CHG$_6$)$_c$— in which $G_6$ is selected from: hydrogen and a hydrocarbyl group with 1 to 10 carbon atoms and c is an integer from 1 to 4. Advantageously, each $G_6$ is H or a hydrocarbyl group that contains 1 to 6 carbon atoms, and more advantageously each $G_6$ is H.

Preferably, at least 50% of the bridging groups Q are independently represented by the formula —(CHG$_6$)$_c$—. Preferably, c is an integer from 1 to 4, wherein each $G_6$ is H or a hydrocarbyl group that contains 1 to 6 carbon atoms, and more preferably each $G_6$ is H.

Advantageously, all Q groups are selected from —(CHG$_6$)$_c$— and c is 1, wherein each $G_6$ is H or a hydrocarbyl group that contains 1 to 6 carbon atoms, and even more preferably each $G_6$ is H.

The reaction product according to the invention can also result from the reaction of at least:
- an alkali and/or alkaline earth metal hydroxybenzoate compound, optionally substituted by a hydrocarbyl group, and optionally overbased,
- a boron compound,
- a polyalkylamine component selected from triamine and tetramine compounds.

The alkali and/or alkaline earth metal hydroxybenzoate compounds, optionally substituted by a hydrocarbyl group, are alkali and/or alkaline earth metal salts of the above-described hydroxybenzoic acid compounds.

The favourite variants of the alkali and/or alkaline earth metal hydroxybenzoate compounds are the same as those related to the hydroxybenzoic acid compounds described above.

According to one variant, the alkali and/or alkaline earth metal hydroxybenzoate compounds are chosen from alkali metal salts.

Preferably, the alkali metal is lithium, sodium or potassium, more preferably potassium.

According to a second variant, the alkali and/or alkaline earth metal hydroxybenzoate compounds are chosen from alkaline earth metal salts.

Preferably, the alkaline earth metal is calcium, barium, magnesium or strontium, more preferably calcium.

According to a specific embodiment, the alkali and/or alkaline earth metal hydroxybenzoate compounds, optionally substituted by a hydrocarbyl group, are overbased.

According to a first variant, the alkali and/or alkaline earth metal hydroxybenzoate compounds are chosen from overbased alkali metal hydroxybenzoate compounds.

Overbased alkali metal alkylhydroxybenzoate compounds may for example be prepared by carboxylation and overbasing of an alkali metal alkylhydroxybenzoate. Such methods are notably disclosed in EP 1 783 134.

According to a second variant, the alkali and/or alkaline earth metal hydroxybenzoate compounds are chosen from overbased alkaline earth metal hydroxybenzoate compounds.

Overbased alkaline earth metal alkylhydroxybenzoate compounds may, for example, be prepared from an alkali metal alkylhydroxybenzoate or directly obtained by overbasing an alkaline earth metal alkylhydroxybenzoate. Methods for the preparation of alkaline earth metal alkylhydroxybenzoate compounds are notably disclosed in EP 2 322 591.

In the reaction with the boron compound and the polyalkylamine component, the hydroxybenzoic acid compound, optionally substituted by a hydrocarbyl group, or the alkali and/or alkaline earth metal salts thereof, can be used as a mixture with an alkylphenol.

According to this variant, the mixture can comprise up to 50% mol of alkylphenol, based on the total number of moles of the mixture of alkylphenol and hydroxybenzoic acid compound, optionally substituted by a hydrocarbyl group, or alkali and/or alkaline earth metal salts thereof. Such mixtures and their preparation are disclosed in, for example, EP 1 783 134 and EP 2 316 823.

The Boron Compound

The boron compound is selected from boric acid, hydrocarbyl boronic acids, boric esters and hydrocarbyl boronic esters, boric oxide, boric acid complexes.

The boron compound can, for example, be selected from: boric acid, boric oxide, boric acid complexes, a trialkyl borate in which the alkyl groups comprise independently from 1 to 4 carbon atoms, a $C_1$-$C_{12}$ alkyl boronic acid, a $C_1$-$C_{12}$ dialkyl boric acid, a $C_6$-$C_{12}$ aryl boric acid, a $C_6$-$C_{12}$ diaryl boric acid, a $C_7$-$C_{12}$ aralkyl boronic acid, a $C_7$-$C_{12}$ diaralkyl boric acid, or products deriving from these by substitution of an alkyl group by one or more alkoxy unit.

Alkyl groups and alkoxy groups can be linear, branched or cyclic.

Boric acid complexes are complexes with a molecule comprising one or more alcohol functionality.

Advantageously, the boron compound is boric acid.

The Polyalkylamine Component

The polyalkylamine component is selected from compounds of formula (IV):

$$\text{R}_2\text{R}_1\text{N}-(\text{CH}_2)_x-\text{NH}-(\text{CH}_2)_y-\text{NH}-[(\text{CH}_2)_z-\text{NH}_2]_a \quad (IV)$$

wherein
a represents either 0 or 1;
x, y, z, represent, independently, an integer selected from 1, 2 or 3.
when a=0, $R_1$, $R_2$ represent, independently, a $C_1$-$C_3$ alkyl group,
when a=1, $R_1$, $R_2$ represent, independently, a group selected from: a hydrogen, and a $C_1$-$C_3$ alkyl group.

According to a favourite embodiment, in formula (IV), x=y.
According to a favourite embodiment, in formula (IV), when a=1, x=y=z.
According to a favourite embodiment, x, y, z, represent, independently, an integer selected from 2 or 3.
According to a first variant, the polyalkylamine component is selected from components of formula (IV) wherein a=0 (triamines components).

According to this variant, the polyalkylamine component is advantageously a di-alkylaminopolyalkylamine responding to formula (IVA):

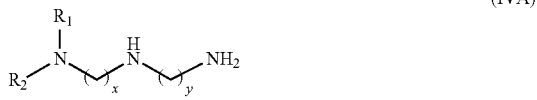
(IVA)

wherein

R$_1$, R$_2$ represent, independently, a C$_1$-C$_3$ alkyl group, x and y are integers representing, independent of each other, either 1, 2, or 3, and the total number of carbon atoms in formula (IVA) is from 4 to 10.

According to a favorite embodiment, in formula (IVA) the total number of carbon atoms in (IVA) is 8.

According to a favorite embodiment, in formula (IVA), R$_1$=R$_2$.

According to a favorite embodiment, in formula (IVA), x=y.

According to a favorite embodiment, in formula (IVA), x=y and represent 2 or 3.

According to a favorite embodiment, in formula (IVA), x=y=3.

According to this embodiment, compound (IV) responds to formula:

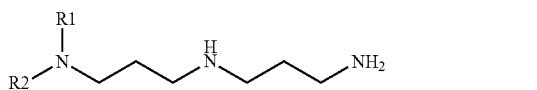

wherein R$_1$, R$_2$ represent, independently, an alkyl moiety with 1 or 2 carbon atoms.

According to a favorite embodiment, in formula (IVA), R$_1$=R$_2$=CH$_3$.

According to a most favorite embodiment, the di-alkylaminopolyalkylamine responding to formula (IV) is dimethylaminopropylaminopropylamine (DMAPAPA):

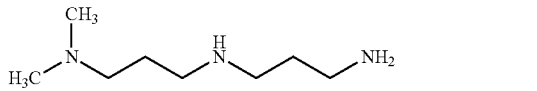

According to a second variant, the amine component is selected from components of formula (IV) wherein a=1 (tetramine components).

According to this variant, the amine component is advantageously a tri-alkylaminopolyalkylamine responding to formula (IVB):

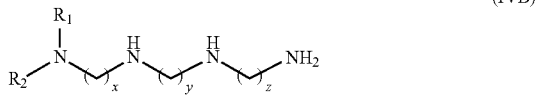
(IVB)

wherein

R$_1$, R$_2$ represent independently a group selected from: a hydrogen, and a C$_1$-C$_3$ alkyl group, and x, y and z are integers representing, independently, either 1, 2, or 3.

According to a favorite embodiment, R$_1$=R$_2$.

According to a favorite embodiment, in formula (IVB), x=y=z.

According to a favorite embodiment, in formula (IVA), x=y=z and represent 2 or 3.

According to a favorite embodiment, in formula (IVB), x=y=z=2.

According to a favorite embodiment, the total number of carbon atoms in (IVB) is from 4 to 15, preferably from 4 to 10, more preferably from 6 to 8.

According to this embodiment, compound (IVB) responds to formula:

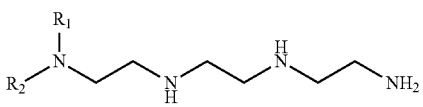

According to a favorite embodiment, in formula (IVB), R$_1$=R$_2$=H.

According to a most favorite embodiment, the tri-alkylaminopolyalkylamine responding to formula (IVB) is triethylenetetramine:

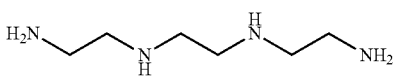

Reaction Product

The reaction of the hydroxybenzoic acid, optionally substituted by a hydrocarbyl, or the alkali and/or alkaline earth metal salt thereof, the boron compound, and the amine component can be effected in any suitable manner.

In the following description of the reaction product, "hydroxybenzoic acid" means "the hydroxybenzoic acid, optionally substituted by a hydrocarbyl group, or the alkali and/or the alkaline earth metal salts thereof".

For example, the reaction can be conducted by first combining hydroxybenzoic acid and the boron compound in the desired ratio and in the presence of a suitable solvent.

Suitable solvents are for example naphtha and polar solvents such as water and an alcohol, like for example: methanol, ethanol, propanol, butanol.

Advantageously, the reaction is conducted with a molar ratio of hydroxybenzoic acid compound:boron compound of from about 30:1 to about 1:30, preferably from 15:1 to 1:5, more preferably from 5:1 to 1:2, even more preferably from 4:1 to 1:1.

After a sufficient time, the boron compound dissolves. Then, the polyalkylamine component is added slowly to the mixture to effect neutralization and formation of the desired reaction product.

Advantageously, the polyalkylamine component is added in amounts such that the molar ratio of hydroxybenzoic acid compound:amine component is from about 30:1 to about 1:30, preferably from 15:1 to about 1:5, more preferably from 5:1 to 1:2, even more preferably from 4:1 to 1:1.

Advantageously, the polyalkylamine component is added in amounts such that the molar ratio of boron compound: amine component is from about 20:1 to 1:20, preferably from 10:1 to 1:10, more preferably from 5:1 to 1:5, even more preferably from 2:1 to 1:2.

The reaction can advantageously be conducted by maintaining the reaction medium at a temperature of from about 20° C. to about 100° C., for example from about 50° C. to about 75° C., generally for a time period ranging from about 0.5 to 5 hours, more preferably from 1 to 4 hours.

After the reaction is completed, the solvent may be evaporated from the reaction medium, preferably, it is evaporated by distillation under vacuum. Alternately, the solvent may remain in mixture with the reaction products which are used as such.

A diluting oil can be added as needed to control viscosity, particularly during removal of solvents by distillation.

The product resulting from this reaction will contain a complex mixture of compounds. The reaction product mixture need not be separated to isolate one or more specific components. Accordingly, the reaction product mixture can be employed as is in the lubrication oil composition of the present invention.

The reaction can be achieved with other reactants in addition to the hydroxybenzoic acid, the boron compound, and the polyalkylamine component.

However, according to the invention, preferably the reaction product results from the reaction of a mixture of reactants (not including the solvent(s)) that consists essentially of at least one hydroxybenzoic acid (optionally hydrocarbyl substituted) or one alkali and/or alkaline earth metal salt thereof, at least one boron compound, and at least one polyalkylamine component as defined above.

Even more preferably, the reaction product results from the reaction of a mixture of reactants (not including the solvent(s)) that consists of at least one hydroxybenzoic acid (optionally hydrocarbyl substituted) or one alkali and/or alkaline earth metal salt thereof, at least one boron compound, and at least one polyalkylamine component as defined above.

Lubricant Composition

The invention is also directed to the use of the reaction products that have been disclosed above as additives in lubricating oil (or lubricant) compositions. It is also directed to the lubricant compositions comprising such additives.

Advantageously, the lubricant composition comprises:
from 80 to 99.9% of at least one base oil,
from 0.1 to 20% of at least one reaction product of at least a hydroxybenzoic acid, optionally hydrocarbyl substituted, or an alkali and/or alkaline metal earth salt thereof, a boron compound, and a polyalkylamine component as defined above,
the percentages being defined by weight of component as compared to the total weight of the composition.

More advantageously, the lubricant composition comprises:
from 85 to 99.9% of at least one base oil,
from 0.1 to 15% of at least one reaction product of at least a hydroxybenzoic acid, optionally hydrocarbyl substituted, or an alkali and/or alkaline metal earth salt thereof, a boron compound, and a polyalkylamine component as defined above,
the percentages being defined by weight of component as compared to the total weight of the composition.

Base Oils

Generally, the lubricating oil compositions according to the invention comprise as a first component an oil of lubricating viscosity, also called "base oils". The base oil for use herein can be any presently known or later-discovered oil of lubricating viscosity used in formulating lubricating oil compositions for any of the following applications, e.g., engine oils, marine cylinder oils, functional fluids such as hydraulic oils, gear oils, transmission fluids, like for example automatic transmission fluids, turbine lubricants, trunk piston engine oils, compressor lubricants, metal-working lubricants, and other lubricating oil and grease compositions.

Advantageously, the lubricant compositions according to the invention are marine engine lubricating oil compositions, preferably they are two-stroke marine engine lubricating oil compositions.

Generally, the oils also called "base oils" used for formulating lubricant compositions according to the present invention may be oils of mineral, synthetic or plant origin as well as their mixtures. The mineral or synthetic oils generally used in the application belong to one of the classes defined in the API classification as summarized below:

| | Saturated substance content (weight percent) | Sulphur content (weight percent) | Viscosity Index |
|---|---|---|---|
| Group 1 Mineral oils | <90% | >0.03% | 80 ≤ VI < 120 |
| Group 2 Hydrocracked oils | ≥90% | ≤0.03% | 80 ≤ VI < 120 |
| Group 3 Hydroisomerized oils | ≥90% | ≤0.03% | ≥120 |
| Group 4 | | PAOs | |
| Group 5 | | Other bases not included in the base Groups 1 to 4 | |

These mineral oils of Group 1 may be obtained by distillation of selected naphthenic or paraffinic crude oils followed by purification of these distillates by methods such as solvent extraction, solvent or catalytic dewaxing, hydrotreating or hydrogenation.

The oils of Groups 2 and 3 are obtained by more severe purification methods, for example a combination of hydrotreating, hydrocracking, hydrogenation and catalytic dewaxing. Examples of synthetic bases of Groups 4 and 5 include poly-alpha olefins, polybutenes, polyisobutenes, alkylbenzenes.

These base oils may be used alone or as a mixture. A mineral oil may be combined with a synthetic oil.

The lubricant compositions of the invention have a viscosity grade of SAE-20, SAE-30, SAE-40, SAE-50 or SAE-60 according to the SAEJ300 classification.

Grade 20 oils have a kinematic viscosity at 100° C. of between 5.6 and 9.3 mm$^2$/s.

Grade 30 oils have a kinematic viscosity at 100° C. of between 9.3 and 12.5 mm$^2$/s.

Grade 40 oils have a kinematic viscosity at 100° C. of between 12.5 and 16.3 mm$^2$/s.

Grade 50 oils have a kinematic viscosity at 100° C. of between 16.3 and 21.9 mm$^2$/s.

Grade 60 oils have a kinematic viscosity at 100° C. of between 21.9 and 26.1 mm$^2$/s.

Preferably, the lubricant composition according to the first aspect and the second aspect is a cylinder lubricant.

The cylinder oils for two-stroke diesel marine engines have a viscosimetric grade SAE-40 to SAE-60, generally preferentially SAE-50 equivalent to a kinematic viscosity at 100° C. comprised between 16.3 and 21.9 mm$^2$/s. Typically, a conventional formulation of cylinder lubricant for two-stroke marine diesel engines is of grade SAE 40 to SAE 60, preferentially SAE 50 (according to the SAE J300 classification) and comprises at least 50% by weight of a lubricating base oil of mineral and/or synthetic origin, adapted to the use in a marine engine, for example of the API Group 1 class. Their viscosity index (VI) is comprised between 80 and 120; their sulphur content is greater than 0.03% and their saturated substance content is less than 90%. The system oils for two-stroke diesel marine engines have a viscosimetric grade SAE-20 to SAE-40, generally preferentially SAE-30 equivalent to a kinematic viscosity at 100° C. comprised between 9.3 and 12.5 mm$^2$/s.

These viscosities may be obtained by mixing additives and base oils for example containing mineral bases of Group 1 such as Neutral Solvent (for example 150 NS, 500 NS or 600 NS) bases and brightstock. Any other combination of mineral, synthetic bases or bases of plant origin, having, as a mixture with the additives, a viscosity compatible with the chosen SAE grade, may be used.

The quantity of base oil in the lubricant composition of the invention is from 30% to 90% by weight relative to the total weight of the lubricant composition, preferably from 40% to 90%, more preferably from 50% to 90%.

In one embodiment of the invention, the lubricant composition has a Base Number (BN) determined according to the standard ASTM D-2896 of at most 70, preferably at most 40, advantageously at most 30 milligrams of potassium hydroxide per gram of the lubricating composition, in particular ranging from 10 to 40, preferably from 15 to 40, more preferably from 25 to 40 milligrams of potassium hydroxide per gram of the lubricant composition.

According to that embodiment, and in a first variant, the lubricant composition according to the invention has a TBN, measured according to standard ASTM D-2896, comprised between 10 and 50 when used for a marine engine, in particular for a four-stroke marine engine and a two-stroke marine engine, preferably for a four-stroke marine engine.

According to that embodiment, and in a second variant, preferably the lubricant composition according to the invention has a TBN, measured according to standard ASTM D-2896, comprised between 20 and 70 when used for a marine engine, in particular for a four-stroke marine engine and a two-stroke marine engine, preferably for a two-stroke marine engine.

In another embodiment of the invention, the lubricant composition has a BN determined according to the standard ASTM D-2896 of at least 50, preferably at least 60, more preferably at least 70, advantageously from 70 to 140.

According to this embodiment, the composition has a high BN (comprised between 70 and 140) and can be used for a marine engine, in particular for a four-stroke marine engine and a two-stroke marine engine, preferably for a two-stroke marine engine.

Additives:

It is optionally possible to substitute the above-described base oils in full or in part by one or more thickening additives whose role is to increase both the hot and cold viscosity of the composition, or by additives improving the viscosity index (VI).

The lubricant composition of the invention may comprise at least one optional additive, chosen in particular from among those frequently used by persons skilled in the art.

In one embodiment, the lubricant composition further comprises an optional additive chosen amongst a neutral detergent, an overbased detergent, an anti-wear additive, an oil soluble fatty amine, a polymer, a dispersing additive, an anti-foaming additive or a mixture thereof.

Detergents are typically anionic compounds containing a long lipophilic hydrocarbon chain and a hydrophilic head, wherein the associated cation is typically a metal cation of an alkali metal or alkaline earth metal. The detergents are preferably selected from alkali metal salts or alkaline earth metal (particularly preferably calcium, magnesium, sodium or barium) salts of carboxylic acids, sulphonates, salicylates, naphthenates, as well as the salts of phenates. These metal salts may contain the metal in an approximately stoichiometric amount relative to the anion group(s) of the detergent. In this case, one refers to non-overbased or "neutral" detergents, although they also contribute to a certain basicity. These "neutral" detergents typically have a BN measured according to ASTM D2896, of less than 150 mg KOH/g, or less than 100 mg KOH/g, or less than 80 mg KOH/g of detergent. This type of so-called neutral detergent may contribute in part to the BN of lubricating compositions. For example, neutral detergents are used such as carboxylates, sulphonates, salicylates, phenates, naphthenates of the alkali and alkaline earth metals, for example calcium, sodium, magnesium, barium. When the metal is in excess (amount greater than the stoichiometric amount relative to the anion groups(s) of the detergent), then these are so-called overbased detergents. Their BN is high, higher than 150 mg KOH/g of detergent, typically from 200 to 700 mg KOH/g of detergent, preferably from 250 to 450 mg KOH/g of detergent. The metal in excess providing the character of an overbased detergent is in the form of insoluble metal salts in oil, for example carbonate, hydroxide, oxalate, acetate, glutamate, preferably carbonate. In one overbased detergent, the metals of these insoluble salts may be the same as, or different from, those of the oil soluble detergents. They are preferably selected from calcium, magnesium, sodium or barium. The overbased detergents are thus in the form of micelles composed of insoluble metal salts that are maintained in suspension in the lubricating composition by the detergents in the form of soluble metal salts in the oil. These micelles may contain one or more types of insoluble metal salts, stabilised by one or more types of detergent. The overbased detergents comprising a single type of detergent-soluble metal salt are generally named according to the nature of the hydrophobic chain of the latter detergent. Thus, they will be called a phenate, salicylate, sulphonate, naphthenate type when the detergent is respectively a phenate, salicylate, sulphonate or naphthenate. The overbased detergents are called mixed type if the micelles comprise several types of detergents, which are different from one another by the nature of their hydrophobic chain. The overbased detergent and the neutral detergent may be selected from carboxylates, sulphonates, salicylates, naphthenates, phenates and mixed detergents combining at least two of these types of detergents. The overbased detergent and the neutral detergent include compounds based on metals selected from calcium, magnesium, sodium or barium, preferably calcium or magnesium. The overbased detergent may be overbased by metal insoluble salts selected from the group of carbonates of alkali and alkaline earth metals, preferably calcium carbonate. The lubricating composition may comprise at least one overbased detergent and at least a neutral detergent as defined above.

Polymers are typically polymers having a low molecular weight of from 2 000 to 50 000 Dalton ($M_n$). The polymers are selected amongst PIB (of from 2 000 Dalton), polyacrylates or polymethacrylates (of from 30 000 Dalton), olefin copolymers, olefin and alpha-olefin copolymers, EPDM, polybutenes, poly alpha-olefin having a high molecular weight (viscosity 100° C.>150), hydrogenated or non-hydrogenated styrene-olefin copolymers.

Anti-wear additives protect the surfaces from friction by forming a protective film adsorbed on these surfaces. The most commonly used is zinc dithiophosphate or ZnDTP.

Also, in this category, there are various phosphorus, sulphur, nitrogen, chlorine and boron compounds. There are a wide variety of anti-wear additives, but the most widely used category is that of the sulphur phospho additives such as metal alkylthiophosphates, especially zinc alkylthiophosphates, more specifically, zinc dialkyl dithiophosphates or ZnDTP. The preferred compounds are those of the formula $Zn((SP(S)(OR_1)(OR_2))_2$, wherein $R_1$ and $R_2$ are alkyl groups, preferably having 1 to 18 carbon atoms. The ZnDTP is typically present at levels of about 0.1 to 2% by weight relative to the total weight of the lubricating composition. The amine phosphates, polysulphides, including sulphurised olefins, are also widely used anti-wear additives. One also optionally finds nitrogen and sulphur type anti-wear and extreme pressure additives in lubricating compositions, such as, for example, metal dithiocarbamates, particularly molybdenum dithiocarbamate. Glycerol esters are also anti-wear additives. Mention may be made of mono-, di- and tri-oleates, monopalmitates and monomyristates. In one embodiment, the content of anti-wear additives ranges from 0.01 to 6%, preferably from 0.1 to 4% by weight relative to the total weight of the lubricating composition.

Dispersants are well known additives used in the formulation of lubricating compositions, in particular for application in the marine field. Their primary role is to maintain in suspension the particles that are initially present or appear in the lubricant during its use in the engine. They prevent their agglomeration by playing on steric hindrance. They may also have a synergistic effect on neutralisation. Dispersants used as lubricant additives typically contain a polar group, associated with a relatively long hydrocarbon chain, generally containing 50 to 400 carbon atoms. The polar group typically contains at least one nitrogen, oxygen, or phosphorus element. Compounds derived from succinic acid are particularly useful as dispersants in lubricating additives. Also used are, in particular, succinimides obtained by condensation of succinic anhydrides and amines, succinic esters obtained by condensation of succinic anhydrides and alcohols or polyols. These compounds can then be treated with various compounds including sulphur, oxygen, formaldehyde, carboxylic acids and boron-containing compounds or zinc in order to produce, for example, borated succinimides or zinc-blocked succinimides. Mannich bases, obtained by polycondensation of phenols substituted with alkyl groups, formaldehyde and primary or secondary amines, are also compounds that are used as dispersants in lubricants. In one embodiment of the invention, the dispersant content may be greater than or equal to 0.1%, preferably 0.5 to 2%, advantageously from 1 to 1.5% by weight relative to the total weight of the lubricating composition. It is possible to use a dispersant from the PIB succinimide family, e.g. boronated or zinc-blocked.

Other optional additives may be chosen from defoamers, for example, polar polymers such as polydimethylsiloxanes, polyacrylates. They may also be chosen from antioxidant and/or anti-rust additives, for example organometallic detergents or thiadiazoles. These additives are known to persons skilled in the art. These additives are generally present in a weight content of 0.1 to 5% based on the total weight of the lubricating composition.

In one embodiment, the lubricant composition according to the invention may further comprise an oil soluble fatty amine.

The fatty amine is of a general formula (VI):

$$R'_1—[(NR'_2)—R'_3]_n—NR'_4R'_5, \qquad (VI)$$

wherein,
$R'_1$ represents a saturated or unsaturated, linear or branched, hydrocarbon group comprising at least 12 carbon atoms, and optionally at least one heteroatom chosen amongst nitrogen, sulphur or oxygen,
$R'_2$, $R'_4$ and $R'_5$ represent independently a hydrogen atom or a saturated or unsaturated, linear or branched, hydrocarbon group comprising optionally at least one heteroatom chosen amongst nitrogen, sulphur or oxygen,
$R'_3$ represents a saturated or unsaturated, linear or branched, hydrocarbon group comprising at least 1 carbon atom, and optionally at least one heteroatom chosen amongst nitrogen, sulphur or oxygen, preferably oxygen,
n is an integer, n is superior or equal to 1, preferably comprised between 1 and 10, more preferably between 1 and 6, notably chosen amongst 1, 2 or 3.

Preferably, the fatty amine is of a general formula (VI), wherein:
$R'_1$ represents a saturated or unsaturated, linear or branched, hydrocarbon group comprising between 12 and 22 carbon atoms, preferably between 14 and 22 carbon atoms, and optionally at least one heteroatom chosen amongst nitrogen, sulphur or oxygen, and/or
$R'_2$, $R'_4$ and $R'_5$ represent independently a hydrogen atom; a saturated or unsaturated, linear or branched, hydrocarbon group comprising between 12 and 22 carbon atoms, preferably between 14 and 22 carbon atoms, more preferably between 16 and 22 carbon atoms; a $(R'_6—O)_p—H$ group wherein $R'_6$ represents a saturated, linear or branched, hydrocarbon group comprising at least 2 carbon atoms, preferably between 2 and 6 carbon atoms, more preferably between 2 and 4 carbon atoms, and p is superior or equal to 1, preferably comprised between 1 and 6, more preferably comprised between 1 and 4; a $(R'_7—N)_p—H_2$ group wherein $R'_7$ represents a saturated, linear or branched, hydrocarbon group comprising at least 2 carbon atoms, preferably between 2 and 6 carbon atoms, more preferably between 2 and 4 carbon atoms, and p is superior or equal to 1, preferably comprised between 1 and 6, more preferably comprised between 1 and 4, and/or
$R'_3$ represents a saturated or unsaturated, linear or branched, alkyl group comprising between 2 and 6 carbon atoms, preferably between 2 and 4 carbon atoms.

In one embodiment, the fatty amine of general formula (VI) represents of from 0.5 to 10%, preferably of from 0.5 to 8% by weight with respect to the total weight of the lubricant composition.

The optional additives such as defined above contained in the lubricant compositions of the present invention can be incorporated in the lubricant composition as separate additives, in particular through separate addition thereof in the base oils. However, they may also be integrated in a concentrate of additives for marine lubricant compositions.

Method for Producing a Marine Lubricant

The present disclosure provides a method for producing a marine lubricant as disclosed above comprising the step of mixing the base oil with the reaction product of at least a hydroxybenzoic acid (optionally hydrocarbyl substituted) or an alkali and/or alkaline metal earth salt thereof, a boron compound, and a polyalkylamine component as defined above, and optionally one or more additive.

Use for Lubricating Engines

The application also relates to the use of a reaction product of at least a hydroxybenzoic acid (optionally hydrocarbyl substituted) or an alkali and/or alkaline metal earth salt thereof, a boron compound, and a polyalkylamine component as defined above for lubricating engines, preferably marine engines. Specifically, the invention is directed to the use of a reaction product of at least a hydroxybenzoic acid (optionally hydrocarbyl substituted) or an alkali and/or alkaline metal earth salt thereof, a boron compound, and a polyalkylamine component as defined above for lubricating two-stroke marine engines and four-stroke marine engines, more preferably two-stroke marine engine.

In particular, the reaction product of at least a hydroxybenzoic acid (optionally hydrocarbyl substituted) or an alkali and/or alkaline metal earth salt thereof, a boron compound, and a polyalkylamine component as defined above is suitable for use in a lubricant composition, as cylinder oil or system oil, for lubricating two-stroke engines and four-stroke marine engines, more preferably two-stroke engines.

The application also relates to a method for lubricating a two-stroke marine engine and a four-stroke marine engine, more preferably a two-stroke marine engine, said method comprising application to said marine engine of the marine lubricant as disclosed above. In particular, the lubricant is applied to the cylinder wall, typically by a pulse lubricating system or by spraying the lubricant onto the piston's rings pack through an injector for lubricating two-stroke engines. It has been observed that applying to the cylinder wall the lubricant composition according to the invention provides increased protection against corrosion, improved engine cleanliness.

The invention claimed is:

1. A product resulting from the reaction of at least:

a hydroxybenzoic acid, optionally substituted by a hydrocarbyl group, or an alkali and/or alkaline earth metal salt thereof, a boron compound, a polyalkylamine component selected from compounds of formula (IV):

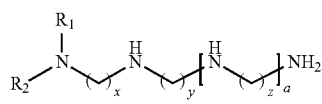

wherein
a represents either 0 or 1;
x, y, z, represent, independently, an integer selected from 1, 2 or 3,
when a=0, $R_1$, $R_2$ represent, independently, a $C_1$-$C_3$ alkyl group,
when a=1, $R_1$, $R_2$ represent, independently, a group selected from: a hydrogen, and a $C_1$-$C_3$ alkyl group.

2. The product according to claim 1, wherein the hydroxybenzoic acid, optionally substituted by a hydrocarbyl group, is selected from mono-alk(en)yl substituted salicylic acids, di-alk(en)yl substituted salicylic acids, acid functionalized calixarenes, notably salicylic acid calixarenes, and mixtures thereof.

3. The product according to claim 1, wherein the hydroxybenzoic acid compound, optionally substituted by a hydrocarbyl group, responds to formula (I):

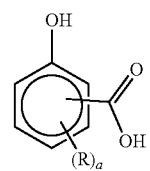

wherein:
R represents a hydrocarbyl group with 1 to 50 carbon atoms, and R can comprise one or more heteroatoms,
a is an integer, a represents 0, 1 or 2.

4. The product according to claim 3, wherein the hydroxybenzoic acid compound, optionally substituted by a hydrocarbyl group, responds to formula (IA):

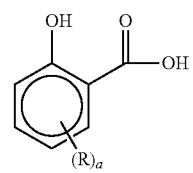

5. The product according to claim 4, wherein the hydroxybenzoic acid compound is salicylic acid.

6. The product according to claim 1, wherein the boron compound is selected from: boric acid, boric acid complexes, boric oxide, a trialkyl borate in which the alkyl groups comprise independently from 1 to 4 carbon atoms, a $C_1$-$C_{12}$ alkyl boronic acid, a $C_1$-$C_{12}$ dialkyl boric acid, a $C_6$-$C_{12}$ aryl boric acid, a $C_6$-$C_{12}$ diaryl boric acid, a $C_7$-$C_{12}$ aralkyl boric acid, a $C_7$-$C_{12}$ diaralkyl boric acid, or products deriving from these by substitution of an alkyl group by one or more alkoxy unit.

7. The product according to claim 6, wherein the boron compound is boric acid.

8. The product according to claim 1, wherein the polyalkylamine component is selected from compounds of formula (IVA):

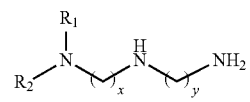

wherein
$R_1$, $R_2$ represent, independently, a $C_1$-$C_3$ alkyl group,
x and y are integers representing, independent of each other, either 1, 2, or 3,
and
the total number of carbon atoms in formula (IVA) is from 4 to 10.

9. The product according to claim 8, wherein $R_1$=$R_2$.

10. The product according to claim 9, wherein $R_1$=$R_2$=$CH_3$.

11. The product according to claim 8, wherein x=y.

12. The product according to claim 11, wherein x=y=3.

13. The product according to claim 1, wherein the polyalkylamine component is selected from compounds of formula (IVB):

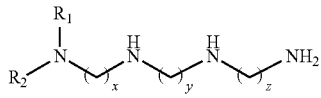

(IVB)

wherein
R$_1$, R$_2$ represent independently a group selected from: a hydrogen, and a C$_1$-C$_3$ alkyl group, and
x, y and z are integers representing, independently, either 1, 2, or 3.

14. The product according to claim 13, wherein R$_1$=R$_2$.

15. The product according to claim 14, wherein R$_1$=R$_2$=H.

16. The product according to claim 13, wherein x=y=z.

17. The product according to claim 16, wherein x=y=z=2.

18. A lubricant composition comprising a product according to claim 1, a base oil and optionally one or more further additives.

19. A method for lubricating a marine engine comprising application to said marine engine of the lubricant composition according to claim 18.

20. The method for lubricating a marine engine according to claim 19, wherein the lubricant composition is applied to the cylinder wall.

\* \* \* \* \*